United States Patent [19]

Arias et al.

[11] Patent Number: 5,281,197

[45] Date of Patent: Jan. 25, 1994

[54] ENDOSCOPIC HEMOSTATIC AGENT DELIVERY SYSTEM

[75] Inventors: Juan J. Arias, Hialeah; Thomas O. Bales, Miami, both of Fla.; David P. Gordon, Stamford, Conn.; Constance M. Ryan, Miami, Fla.; Frank A. Scarfone, Boca Raton, Fla.; Kevin W. Smith; David Turkel, both of Miami, Fla.

[73] Assignee: Symbiosis Corporation, Miami, Fla.

[21] Appl. No.: 919,893

[22] Filed: Jul. 27, 1992

[51] Int. Cl.$^5$ .......................................... A61M 31/00
[52] U.S. Cl. ..................................... 604/57; 604/60; 604/209
[58] Field of Search ............... 604/57, 59–64, 604/209, 210; 128/DIG. 8

[56] References Cited

U.S. PATENT DOCUMENTS

| | | | |
|---|---|---|---|
| 3,110,310 | 11/1963 | Cislak | 604/209 |
| 4,086,914 | 5/1978 | Moore | 604/64 |
| 4,154,239 | 5/1979 | Turley | 604/62 |
| 4,361,150 | 11/1982 | Voss | 604/59 |
| 4,406,654 | 9/1983 | Bristow | 604/209 |
| 4,700,692 | 10/1987 | Baumgarter | 604/63 |
| 4,790,819 | 12/1988 | Li et al. | 604/59 |
| 4,846,793 | 7/1989 | Leonard et al. | 604/62 |
| 5,021,059 | 6/1991 | Kensey et al. | 604/60 |
| 5,222,939 | 6/1993 | Tiefenbrun et al. | 604/57 |

FOREIGN PATENT DOCUMENTS

| | | | |
|---|---|---|---|
| 139836 | 2/1949 | Australia | 604/61 |
| 245802 | 8/1960 | Australia | 604/64 |
| 651524 | 4/1951 | United Kingdom | 604/59 |
| WO92/20312 | 11/1992 | World Int. Prop. O. | |

Primary Examiner—Ralph Lewis
Attorney, Agent, or Firm—David P. Gordon

[57] ABSTRACT

An endoscopic tool for dispensing units of hemostatic agent broadly comprises a hollow tube which holds a plurality of individual units of the hemostatic agent, a valve at the distal end of the hollow tube which permits the hemostatic agent to pass therethrough but prevents foreign matter from contacting the hemostatic agent while in the tube, a plunger which extends into the hollow tube and contacts a proximal unit of the hemostatic agent, and a mechanism for moving the plunger distally in incremental movements to cause, upon each incremental movement, an individual unit of the hemostatic agent to be pushed through the valve. Typically, the mechanism for moving the plunger and the proximal end of the hollow tube are held in a handle. One mechanism for moving the plunger utilizes a portion of the plunger as a ratchet by forming a plurality of conical elements thereon, and utilizes a switch in the handle which has a V-spring coupled thereto as a pawl for advancing the conical elements. A second mechanism utilizes a regularly shaped notched cutout in the handle as the ratchet, and a vertical protrusion on the plunger which extends through the cutout as an engagement element. The notched cutout provides resilient stops, and the protrusion is shaped to allow it to be forced in a forward direction through each resilient stop and then to sit in another notch.

19 Claims, 3 Drawing Sheets

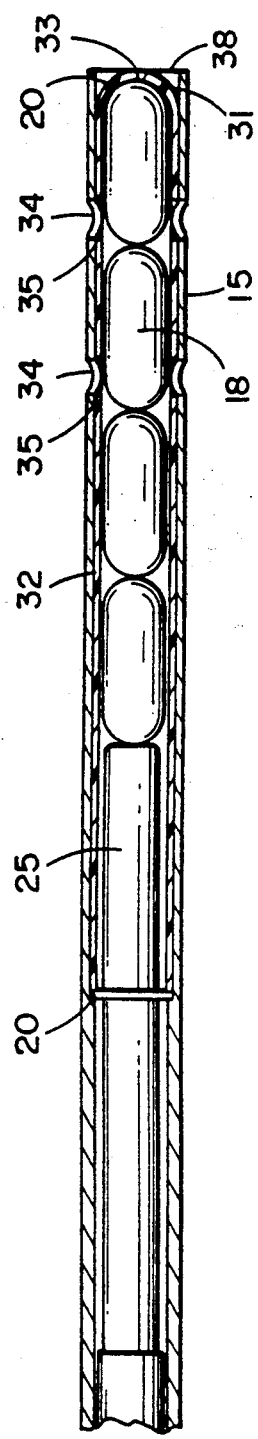
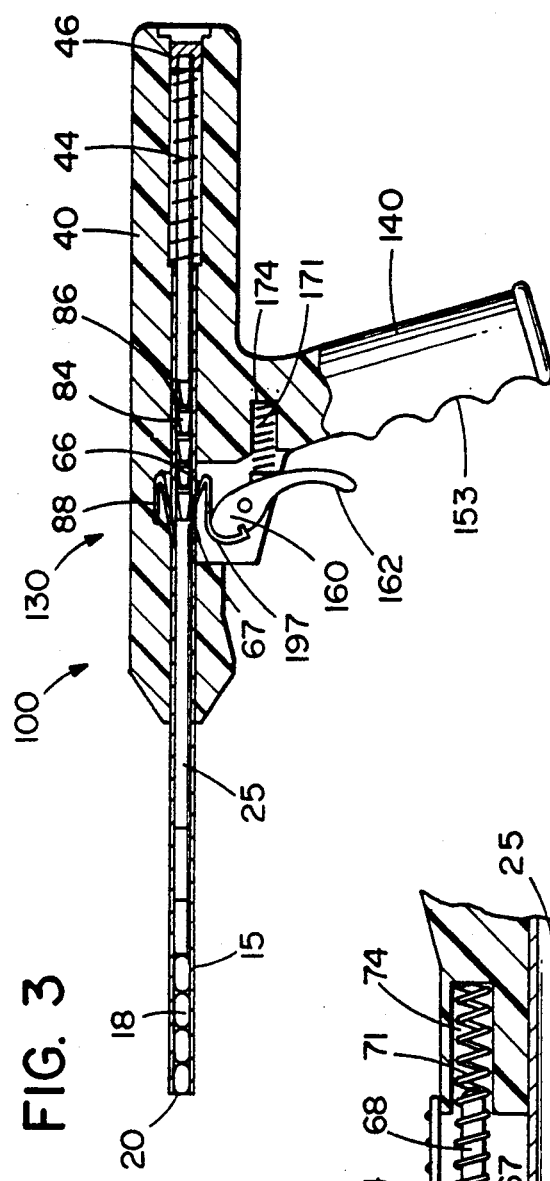
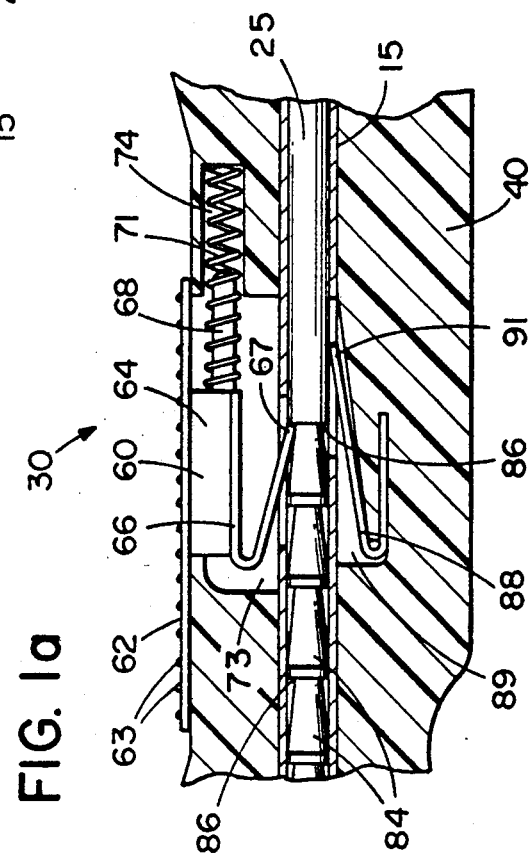

ENDOSCOPIC HEMOSTATIC AGENT DELIVERY SYSTEM

BACKGROUND OF THE INVENTION

This invention generally relates to endoscopic instruments. The invention more particularly relates to endoscopic instruments for delivering a hemostatic agent to the site of internal bleeding, and methods relating to the same.

Several hemostatic agents are known and used to stop bleeding. Most useful and common among the known agents are those containing collagen fibrils. U.S. Pat. No. 3,742,995 to Battista et al. discloses a "Fibrous Collagen Derived Product Having Hemostatic and Wound Binding Properties". Battista et al. teach the production of dressing containing collagen for use on wounds as a hemostatic agent. Battista et al., however, do not address the delivery of such a hemostatic agent through an endoscopic instrument.

There are many other references in the prior art to the use of collagen as a hemostatic agent. Most of these references refer to the production of fibrous collagen as derived from various biological tissues as animal skins, placentas, or the like, and the combination of collagen with other substances to improve its hemostatic properties. For example, U.S. Pat. No. 4,749,689 to Miyata-Teruo et al. discloses a "Hemostatic Agent Composed of Collagen/Gelatin and Protamine" which is claimed to stop bleeding faster than a conventional agent made of pure collagen.

Collagen containing hemostatic agents are presently widely available either in non-woven webs or in jars of fibrous material. AVITENE, a trademark of MedChem Products, Inc., Wodburn, Mass., is one such product. AVITENE is available in sheets 1 mm thick and in jars of fibrous material.

Collagen has also been used as a hemostatic agent to stop internal bleeding during surgery. Moreover, while not admitted as prior art to the present invention, it is presently known to deliver a hemostatic agent to the site of internal bleeding using an endoscopic-type instrument. One such instrument in use today (Endo-Avitene TM) is sold by MedChem Products, Inc. and generally comprises a thin tube packed with fibrous collagen hemostat and fitted with a sliding syringe-like plunger which pushes the fibrous hemostat through the tube. The ability to delivery the hemostatic agent to the internal bleeding site provides advantages in endoscopic surgery in that electrosurgical techniques such as cautery and laser techniques sometimes can be avoided. The electrosurgical techniques, while certainly helpful, have the risk of lateral tissue damage and alternate site burns. While modern electrosurgical devices are designed to minimize these risks, the risks have not been eliminated. Even modern surgical lasers can produce lateral tissue damage or inadvertently pierce or burn delicate tissue.

While the Endo-Avitene TM product sold by Med-Chem Products, Inc. is useful for its purposes, it has several drawbacks. In use, the device which has a long open tube which is partly filled with collagen is inserted through a 10 mm trochar tube and positioned at the bleeding site. Because the collagen containing tube is open, however, the application of the collagen can become complicated, as during dispensing and cutting, the collagen could become wetted by blood resulting in an adherent mass at the end of the tube. Also, when the plunger of the device is depressed, the collagen is delivered as a continuous fibrous string. After a sufficient amount of collagen has been dispensed, it must be cut off from the continuous string with endoscopic scissors. However, the necessity of cutting the collagen to the desired size slows the actual application of the collagen to the bleeding site and actually increases the risk of accidentally cutting delicate tissue. Moreover, it is extremely difficult to both control and measure accurately the amount of the hemostat dispensed. In fact, it is quite possible that too much hemostat would be delivered, thereby unduly complicating the surgical procedure. While it would be possible to repetitively re-load the Endo-Avitene TM product with a very small amount of hemostat, such an approach would be time consuming and might require that the tool be removed from and reinserted into the trochar tube. Reinsertion also introduces additional dangers besides the difficulty of locating the tool at the proper location. In fact, once inserted, it is desirable that the tool not be removed and reused, due to possible contamination problems.

SUMMARY OF THE INVENTION

It is therefore an object of the invention to provide an endoscopic tool from which small measured amounts of hemostatic agent are dispensed without the necessity of cutting the hemostatic agent.

It is another object of the invention to provide an endoscopic hemostatic agent delivery system which provides small amounts of hemostatic agent to the site of internal bleeding.

It is a further object of the invention to provide a disposable hemostatic agent delivery system where incremental quantities of hemostatic agent are controllably delivered to an internal bleeding site.

Another object of the invention is to provide a hemostatic agent dispenser tool where incremental quantities of hemostatic agent are controllably delivered to a bleeding site but are protected from contact with blood or foreign matter prior to delivery.

A further object of the invention is to provide a hemostatic agent dispenser tool for insertion through a trocar tube which utilizes a ratchet type mechanism for delivering individual pieces of hemostatic agent such as collagen to a surgical site.

Yet another object of the invention is to provide a method for controlling bleeding at internal bleeding sites using a hemostatic agent dispenser tool which controllably delivers individual pieces of hemostatic agent.

In accord with the objects of the invention, the hemostatic agent dispenser tool of the invention broadly comprises a hollow tube which holds a plurality of individual units of the hemostatic agent, a valve at the distal end of the hollow tube for permitting the hemostatic agent to pass therethrough but to prevent blood and foreign matter from contacting the hemostatic agent while in the tube, a plunger which extends into the hollow tube and contacts a proximal unit of the hemostatic agent, and mechanical means for moving the plunger distally in incremental movements to cause, upon each incremental movement, an individual unit of the hemostatic agent to be pushed through the valve. Typically, the mechanical means for moving the plunger and the proximal end of the hollow tube are held in a handle.

In the preferred embodiments, the mechanical means for moving the plunger comprises any of several ratchet-type mechanisms. A first ratchet-type mechanism utilizes a portion of the plunger as a ratchet by forming a plurality of conical elements thereon, and utilizes a switch in the handle which has a V-spring coupled thereto as a pawl for advancing the conical elements. When the switch is in a first position, the end of the V-spring pawl sits on the back face of a conical element. Movement of the switch to a second forward position causes the V-spring to advance the conical element and hence the plunger forward, thereby dispensing a unit of hemostatic agent through the valve. Movement of the switch back to the first position causes the V-spring to ride over the next conical element of the plunger with the end of the V-spring eventually seating on the back face of that conical element. Dispensing of another unit of hemostatic agent is then accomplished by movement of the switch to the forward position.

A second ratchet-type mechanism utilizes a regularly shaped notched cutout in the handle as the ratchet, and a vertical protrusion on the plunger which extends through the cutout as an engagement element. The notched cutout provides resilient stops, and the protrusion is shaped to allow it to be forced in a forward direction through each resilient stop and then to sit in another notch. Each time the protrusion is forced through a stop and into another notch, another unit of the hemostatic agent is dispensed. With this second ratchet-type mechanism, the location of the plunger protrusion in the notched handle provides the user with information as to the number of hemostatic agent units which have been dispensed and which are left for dispensing.

Additional objects and advantages of the invention will become apparent to those skilled in the art upon reference to the detailed description taken in conjunction with the provided figures.

BRIEF DESCRIPTION OF THE DRAWINGS

FIGS. 1a and 1b are enlarged views of portions of FIG. 1;

FIG. 3 is a second embodiment of the hemostatic agent dispenser tool of the invention utilizing a trigger mechanism for dispensing the hemostatic agent;

DETAILED DESCRIPTION OF THE PREFERRED EMBODIMENTS

Figure 1:
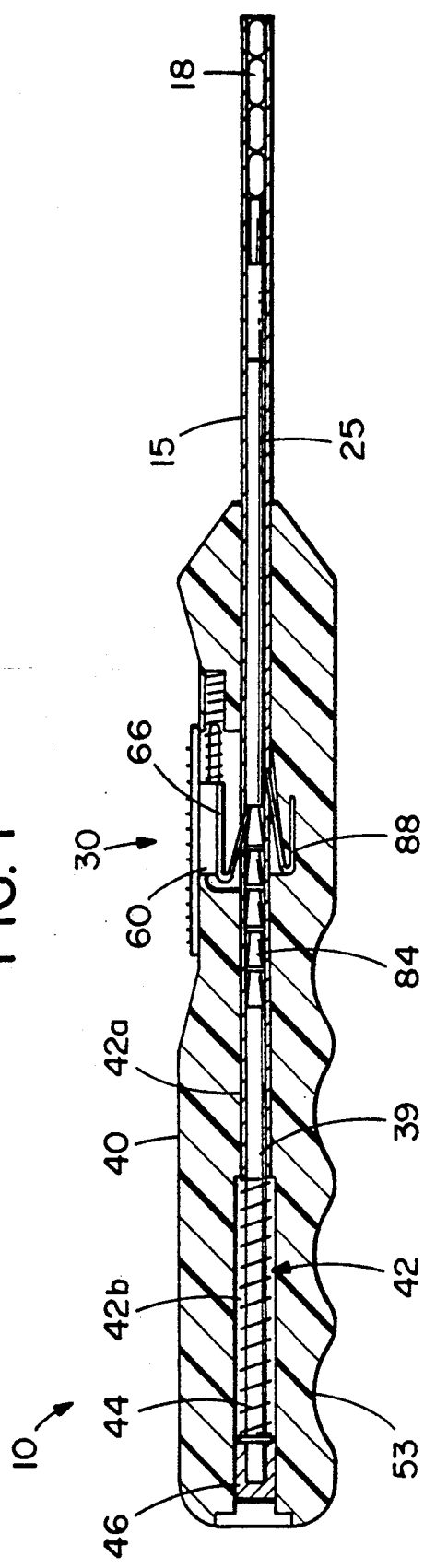
FIG. 1 is a sectional view of a first embodiment of the hemostatic agent dispenser tool of the invention.

Turning to FIGS. 1, 1a, 1b, and 2, a first hemostatic agent dispenser tool 10 in accord with the invention is seen. The primary components of the tool 10 a hollow tube 15 which holds and dispenses a plurality of individual units of the hemostatic agent 18 such as collagen, a valve 20, a plunger 25, and a mechanism 30 for moving the plunger distally in incremental movements. While the valve 20 can be of any of many types of check valves (e.g., slit valves, flapper valves, etc.), in accord with a preferred embodiment of the invention, as seen in FIG. 1b, valve 20 is a substantially condom-shaped plastic valve, with a rounded end 31 which effectively closes off the distal opening 38 in the hollow tube, and a long sleeve 32. The rounded end 31 of the valve 20 has a slit 33 therein, and is shaped to accommodate oblong pellets of collagen or other hemostatic agent 18 which are forced through the slit 33 as described hereinafter. The long sleeve 32 of the valve 20 sits inside hollow tube 15, and preferably includes nubs or protrusions 34 which extend into holes 35 in the hollow tube 15 thereby holding the valve 20 in place. Preferably, the long sleeve 32 of the valve 20 is also bonded to the hollow tube 15 which may be formed of plastic or metal as desired. Regardless of the manner in which it is held in the hollow tube 15, valve 20 functions to permit the hemostatic agent 18 to pass therethrough and out of hollow tube 15, but prevents foreign matter (such as blood) from contacting the hemostatic agent 18 while it is in the hollow tube 15.

As aforementioned, the distal end 38 of the hollow tube 15 is open. The proximal end 39 of the distal tube is likewise open and is preferably insert molded into a handle 40. Handle 40, as seen in FIG. 1 has a passage 42 which extends axially therethrough through which the collagen pellets 18 and the plunger 25 are loaded. Passage 42 includes a narrower passage 42a which receives the hollow tube 15, and a slightly larger passage 42b which receives a spring 44 and a plug 46. Spring 44 is fixed to plug 46 which plugs the proximal end of the handle 40 and also extends around and is fixed to the proximal end of the plunger 25. By being fixed to the plunger 25 and to the plug 46, spring 44 applies a force on the plunger 25 which prevents the plunger from accidentally discharging hemostatic agent pellets 18 by shaking or by sharp downwards movement.

Figure 2:
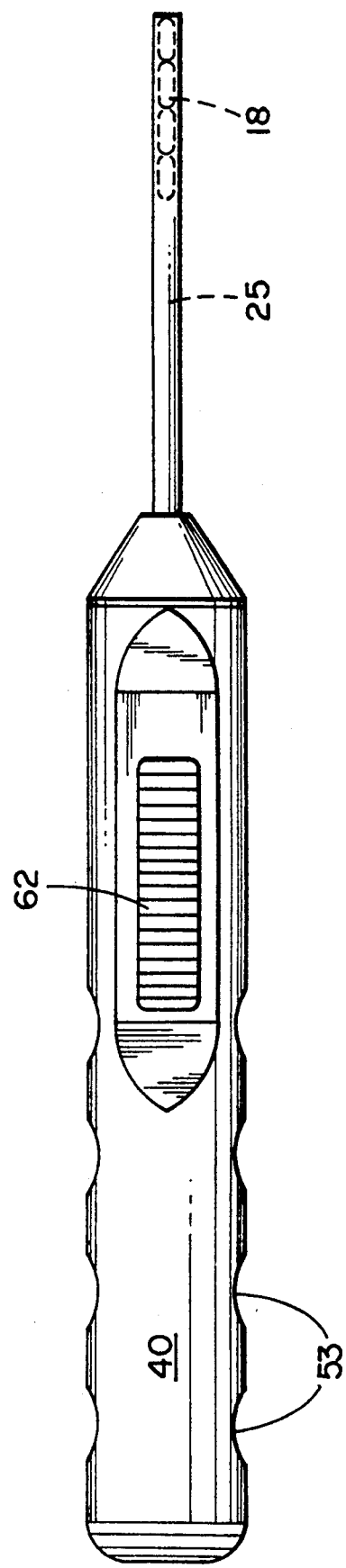
FIG. 2 is a top plan view of the tool of FIG. 1.
Figure 4A:
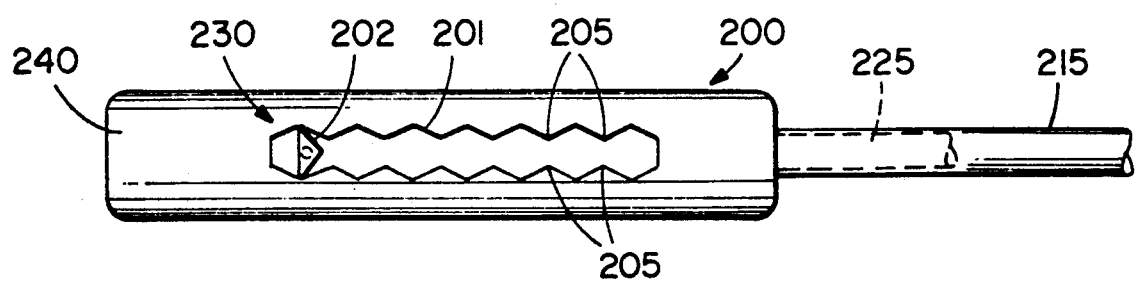
FIGS. 4a and 4b are respectively schematic top and sectional partial views of a third embodiment of the hemostatic agent dispenser tool of the invention, with the plunger located in an initial position.
Figure 4B:
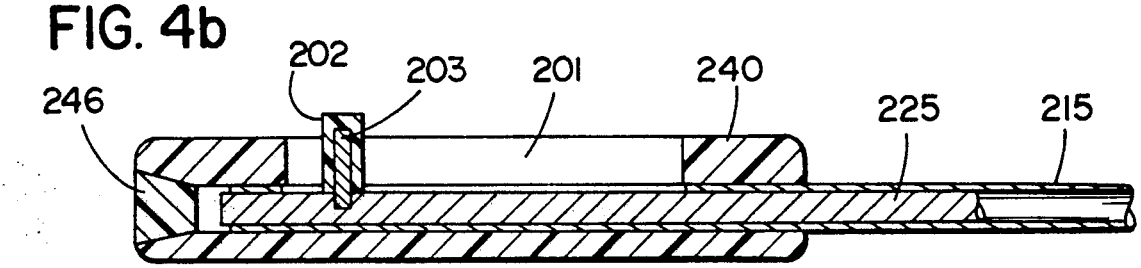
Figure 5A:
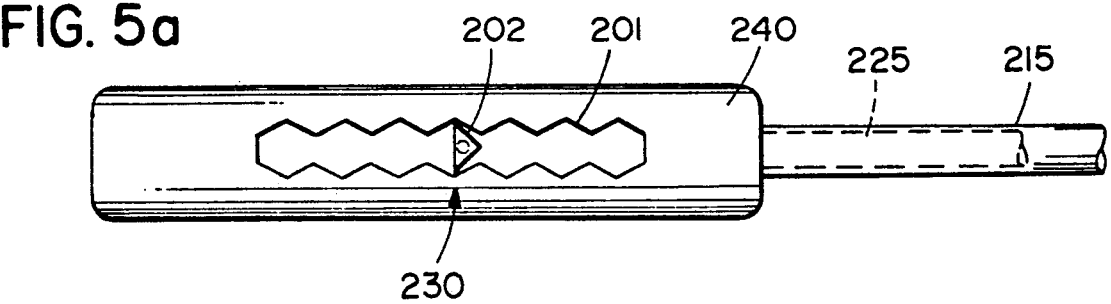
FIGS. 5a and 5b are respectively schematic top and sectional partial views of the tool of FIGS. 4a and 4b showing the position of the plunger after three units of hemostatic agent have been dispensed.
Figure 5B:
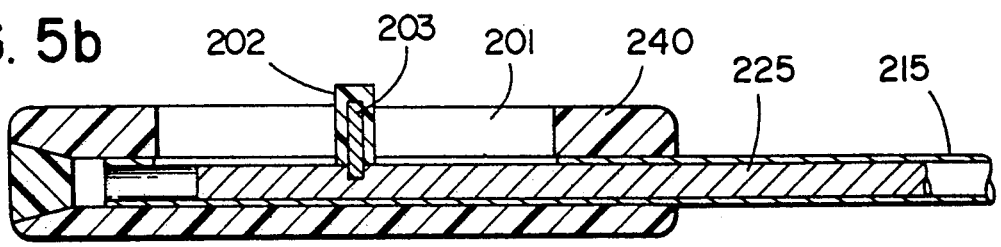

As seen in FIGS. 1 and 2, handle 40 is preferably provided with finger grips 53 along its bottom surface. Also housed in handle 40 is the mechanism 30 for moving the plunger distally in incremental movements. Mechanism 30 is best understood with reference to FIG. 1a.

Turning to FIG. 1a, it is seen that mechanism 30 is effectively a ratchet and pawl mechanism with the ratchet being integral with the plunger 25 as hereinafter described, and the pawl being coupled to a slide switch mechanism 60. In particular, the slide switch 60 mechanism includes an external slide element 62 having nubs 63, a base element 64 which is fixedly attached to the slide element 62, a V-spring element 66, with one side of the V fixedly attached to the base of base element 64 and with free end 67 extending at an angle thereto, a finger 68 extending axially from the base element, and a coil spring 71 seated on the front of the base element 64 and extending around and past the finger 68. As shown, handle 40 has a cutout 73 for the base, spring and finger elements of slide switch 60. The cutout also includes tunnel 76 into which the coil spring 68 extends and is affixed and into which finger 68 can extend when switch 60 is moved forward.

In the embodiment of FIGS. 1 and 1a, the ratchet of the advancing mechanism 30 is the formation in a proximal portion of the plunger of a series of conical shaped elements 84 which are preferably molded into the plunger during formation thereof. Each conical shaped element has a front distal portion which is of smaller diameter than its rear proximal portion. Thus, a seat 86 is formed where the smaller distal portion of one conical element meets the larger proximal portion of another conical element. As seen in FIG. 1a, the free end 67 of the V-spring element 66 of slide switch 60 is arranged to abut seat 86. In this manner, when switch 60 is moved forward by pushing slide element 62, V-spring 66 acts as a pawl and pushes on seat 86 of plunger 25. As the plunger 25 moves forward, it pushes the capsules 18, and discharges a capsule 18 through valve 20. As it is pushed forward, the finger 68 of the switch 60 extends into tunnel 76, and spring 71 is compressed. Upon release of switch 60, the switch 60 is forced backward by spring 68 (and/or by finger movement of the slide 62), and the end 67 of V-spring 66 rides up over the ramped conical surface of the adjacent cone element 84, coming to rest at a new seat 86. To discharge another unit of hemostatic agent, all that is required is that slide switch 60 be moved forward again. Because the conical elements 84 are arranged to be the same size as the hemostatic agent units 18, each forward movement of slide switch 60 moves the plunger 25 incrementally, thereby discharging a single unit of hemostatic agent 18.

As previously mentioned, after a unit of hemostatic agent 18 has been discharged from tool 10, movement of switch 60 backward causes spring 66 to ride over the adjacent conical element 84 of the plunger and to reset into a new seat 86. In order to avoid movement of the plunger backward due to friction as the spring 66 moves over the conical element 84, an additional V-spring 88 is preferably provided in another cutout 89 of handle 40. Spring 88 is fixed relative to handle 40 and the free end 91 of spring 88 is located approximately the length of one conical element 84 away from the end 67 of spring 66 when slide switch 60 is in its back position. With the provided arrangement, when switch 60 is moved forward, the end 91 of spring 88 will set in seat 86 and hold the plunger 25 in position as switch 60 is moved backward and spring 66 rides over the adjacent conical element 84.

In FIG. 3, a second embodiment of the hemostatic agent tool of the invention is seen. In tool 100, parts which are the same as in tool 10 are provided with the same descriptive numbers, while parts which have similar function are provided with numbers one hundred removed from similar parts of tool 10. Thus, tool 100 is provided with a tube 15, having a valve 20 at its distal end, a plunger 25, and a mechanism 130 for moving the plunger 25 in incremental movements. Mechanism 130 is very similar to mechanism 30 in that it includes conical elements 84 on the plunger, and a spring 66 in housing 40 having a free end 67 which sets on the back face of the conical elements 84. The primary difference between the embodiment of tool 100 and tool 10 is that tool 100 is provided with a pistol type handle 140 with grips 153 and a trigger mechanism 160 having a trigger 162 which is pushed against spring 171 housed in tunnel 174. As the trigger 162 is pulled backward toward handle 140, the top portion 197 of the trigger 162 to which the spring 66 is coupled moves forward (distally) in the housing 40. This forward movement causes spring end 67 to push the plunger 25 forward and cause a unit of hemostatic agent 18 to be pushed through Valve 20. Upon release of the trigger 162, the trigger 152 is pushed forward away from handle 140 by spring 171, and the top 197 of trigger moves backward (proximally). In turn, spring 66 rides over its adjacent conical element 84 and seats in the next seat 86, with spring 88 ensuring that plunger 25 is not moved backward at the same time.

The mechanism 230 for moving a plunger 225 of a third embodiment 200 of the hemostatic agent delivery tool is seen in FIGS. 4a, 4b, and 5a, and 5b (the distal end of tool 200 preferably being identical to the embodiments of FIGS. 1-3). As shown, mechanism 230 comprises the combination of a notched cutout 201 in the handle 240 of the tool 200 in conjunction with the proximal end portion of the plunger 225 which is provided with a knob or protrusion 202 which extends perpendicular to the plunger 225 and through cutout 201. The notched cutout 201 is shaped with a plurality of resilient stops 205 (typically formed during molding) through which the knob 202 can be forced. Each notch is preferably the length of a unit of hemostatic agent. Thus, as the knob 202 is forced past one resilient stop 205 and from one notch into another, a single unit of hemostatic agent is released from the tube 215. As shown in FIGS. 4a, 4b, 5a, and 5b, the tube 215 extends through the housing 240 and is closed by stopper 246. With this arrangement, tube 215 must also have an opening through which knob 202 extends. However, if desired, the proximal end of tube 215 can terminate at the distal end of the handle 240. A passage through the handle is then preferably provided so that the hemostatic agent and plunger may be loaded during assembly. Knob 202 can be integrally formed with the plunger 225, or, as shown, can be attached to the plunger via the use of a screw 203 or the like which extends through the knob 202 and into the plunger 225. Knob 202 is also preferably tapered such that it widens as it extends from its distal end to its proximal end. Because the cutout is notched with wider sections and narrower resilient stops 205, the tapering of knob 202 permits the knob 202 to be forced through the resilient stops 205 in the forward direction only; the tapering distal surface of knob 202 acting as a wedge to force resilient stops 205 open, but the flat proximal surface of knob 202 being unable to be forced through resilient stops 205. This arrangement eliminates the need for means for preventing backward movement of the plunger after each incremental movement of the plunger. It also eliminates the need for means for restraining forward movement of the plunger.

It will be appreciated by those skilled in the art, that with the plunger movement mechanism 230 of FIGS. 4a, 4b, 5a and 5b, the practitioner will be able to determine the number of hemostatic agent units that have been dispensed and the number of units left in the tool 210. Thus if tool 210 is provided with six units (cutout 201 being provided with six stops), after dispensing of three units of hemostatic agent, knob 202 would be in the position shown in FIG. 5a and 5b. By looking at the position, the practitioner would know that three units were dispensed, and three more units were left to be dispensed. In fact, if desired, unit indication numbers (not shown) could be provided on the top surface of the handle so that the determination need not be made by eye.

While hemostatic agent pellets are shown in FIGS. 1 and 1b and have been described for use with all of the embodiments, it will be appreciated that the "pellets" can take various forms. By way of example only and not by way of limitation, the pellets may be formed of molded hemostatic agent or may be made by rolling a sheet of hemostatic agent fiber.

Figure 6:
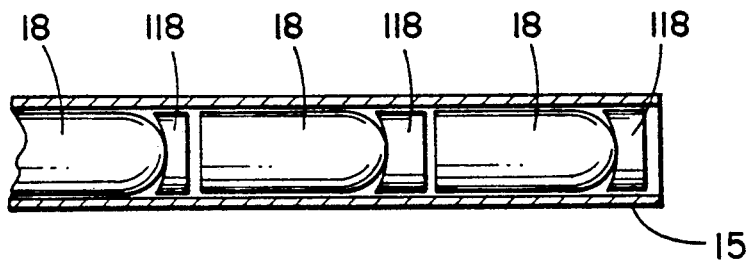
FIG. 6 is a schematic view of the distal end of a hemostatic agent dispenser tool where the hemostatic agent pellets are separated by inert spacers.

Turning to FIG. 6, and according to another aspect of the invention, each unit 18 of hemostatic agent may be separated by an attached or separate inert bioabsorbable or dissolvable spacer element 118. The function of spacer element 118 is to protect the hemostatic agent unit 18 from contact with blood or other foreign material prior to dispensing. It will be appreciated that the inert spacer element 118 may be used in conjunction with the valve 20 or may be used in lieu thereof as the protective mechanism for the hemostatic agent units 18. When using without the valve, there is no preferred shape for the units; i.e., the pellet shape is not necessarily advantageous. Regardless, in using the spacer elements 118, account must be taken for the total axial length of the spacer element and the hemostatic agent unit when determining the distance that the plunger must be incrementally moved.

It will be appreciated that the method of the invention relates directly to the apparatus and involves applying individual units of a hemostatic agent to an internal bleeding site by moving the plunger in measured incremental movements in order to dispense the individual units of the hemostatic agent.

There have been illustrated and described herein endoscopic hemostatic agent delivery systems. While particular embodiments of the invention have been described, it is not intended that the invention be limited thereto, as it is intended that the invention be as broad in scope as the art will allow and that the specification be read likewise. Thus, while particular mechanisms for incremental movement of the plunger were disclosed, it will be appreciated that other mechanisms could be utilized. For example, instead of the disclosed slide switch, trigger, and knob, a thumbwheel or crank could be utilized to incrementally advance the plunger. Also, while a particular type of valve at the distal end of the tool was described, it will be appreciated that other valves could be utilized. Likewise, while collagen was described as the preferred hemostatic agent, it will be appreciated that other hemostatic agents could be utilized, and while tools holding six units or pellets of hemostatic agent were shown, it will be appreciated that any reasonable number of units could be held in the tool, provided that the mechanism for dispensing the units is capable of that many incremental movements. Further, while elements of the disclosed preferred tools were described as having certain shapes, and were further described as being made of certain materials, it will be appreciated that other materials and shapes can be utilized. For example, while the hollow tube was described as preferably comprised of a metal, it will be appreciated that for certain endoscopic procedures, it may be preferable that the hollow tube (and the plunger) be bendable, and hence a flexible material such as any of numerous plastics known in the art might be utilized. Similarly, while the tool embodiment utilizing the knob and the notched cutout was shown as a knob with a tapered horizontal cross-section, and an alternately widening and narrowing cutout, it will be appreciated that different shaped knobs and cutouts could be effectively utilized to obtain the same desired results. It will therefore be appreciated by those skilled in the art that yet other modifications could be made to the provided invention without deviating from its spirit and scope as so claimed.

We claim:

1. An endoscopic tool comprising:

a) a hollow tube containing a plurality of discrete units of hemostatic agent, said hollow tube having proximal and distal ends with an opening in said distal end;

b) a plunger which extends into the hollow tube and contacts a proximal unit of said hemostatic agent; and c) hand actuated movement means coupled to said plunger for moving said plunger distally in measured incremental movements to cause, upon each said incremental movement, at least one of said discrete units of said hemostatic agent to be pushed out of said hollow tube through said opening in said distal end of said hollow tube, wherein said plunger and said hand actuated movement means together comprise a ratchet means having means for preventing proximal movement of said plunger upon each said incremental movement.

2. An endoscopic tool according to claim 1, further comprising:

d) a valve at said distal end of said hollow tube, said valve permitting said hemostatic agent to pass therethrough but preventing foreign matter from contacting said hemostatic agent while said hemostatic agent is in said hollow tube.

3. An endoscopic tool according to claim 2, further comprising: a handle, said handle housing said said proximal end of said hollow tube and said hand actuated movement means.

4. An endoscopic tool according to claim 1, further comprising: a handle, said handle housing said said proximal end of said hollow tube and said hand actuated movement means.

5. An endoscopic tool according to claim 4, wherein: said hand actuated movement means comprises a cutout in said handle having a plurality of resilient stops and hand-grippable means coupled to said plunger and extending through said cutout, said hand-grippable means being shaped relative to said cutout such that said hand-grippable means can be forced past said resilient stops of said handle.

6. An endoscopic tool according to claim 5, wherein: said cutout in said handle comprises a plurality of notches of wider diameter separated by said plurality of resilient stops of smaller diameter, and said hand-grippable means comprises a knob tapered down in cross-section as it extends distally, wherein said knob acts as a wedge for forcing through a resilient stop as it is pushed distally.

7. An endoscopic tool according to claim 6, wherein: each said notch has an axial length substantially equal to the length of the unit of hemostatic agent.

8. An endoscopic tool according to claim 7, wherein: said plurality of notches comprises a number equal to or greater than the number of units of hemostatic agent contained in said tube.

9. An endoscopic tool according to claim 8, further comprising:

a valve at said distal end of the hollow tube, said valve permitting the hemostatic agent to pass therethrough but preventing foreign matter from contacting the hemostatic agent while the hemostatic agent is in said hollow tube.

10. An endoscopic tool according to claim 1, further comprising:

d) a plurality of spacer means which are insert relative to blood, wherein said plurality of discrete units of said hemostatic agent and said inert spacer means are arranged in a line with a first spacer means at said distal end of said hollow tube, followed by a first of said discrete units of said hemostatic agent, followed by a second spacer means, followed by a second of said discrete units of said hemostatic agent.

11. An endoscopic tool according to claim 1, wherein:
said plunger has a proximal portion having a plurality of ramps and seats, each said ramp increasing in diameter as it extends proximally, and each said ramp terminating in a said seat, and
said hand actuated movement means comprises said proximal portion of said plunger and a pawl means for contacting a first seat of said proximal portion of said plunger and for pushing said first seat forward a predetermined distance.

12. An endoscopic tool according to claim 11, wherein:
said pawl means comprises a switch having a finger-actuated portion and a V-spring having a first portion coupled to said finger-actuated portion and a second portion angled at an angle similar to said ramp of said plunger and having a free end contacting said first seat.

13. An endoscopic tool according to claim 12, further comprising:
a valve at said distal end of the hollow tube, said valve permitting the hemostatic agent to pass therethrough but preventing foreign matter from contacting the hemostatic agent while the hemostatic agent is in said hollow tube.

14. An endoscopic tool according to claim 7, wherein:
said tool further comprises a handle, said handle housing said said proximal end of said hollow tube and said hand actuated movement means, and
said pawl means comprises
a slide switch having a finger actuated slide element external a surface of said handle and a base element coupled to said slide element and located internally of said surface of said handle, said slide switch movable within said handle from a first position to a second position, and a V-spring having one portion fixedly coupled to said base element of said slide switch and having a second portion with a free end, wherein
movement of said slide switch from said first position to said second position causes said free end of said V-spring to push on a first seat of said proximal portion of said plunger and push said plunger distally a first predetermined distance, and movement of said slide switch from said second position to said first position causes said V-spring to ride over an adjacent ramp of said proximal portion of said plunger and to set in a second seat of said proximal portion of said plunger.

15. An endoscopic tool according to claim 14, wherein:
said means for preventing proximal movement comprises means fixed to said handle and unable to move relative thereto, said means fixed to said handle having means for engaging a seat of said proximal portion of said plunger.

16. An endoscopic tool according to claim 11, wherein:
each said ramp has an axial length substantially equal to the length of the unit of hemostatic agent.

17. An endoscopic tool according to claim 11, wherein:
said tool further comprises a handle, said handle housing said said proximal end of said hollow tube and said hand actuated movement means, and
said pawl means comprises
a finger actuated trigger means having a first portion which is external a surface of said handle and a second portion which is internal said surface of said handle, said trigger means being movable within and relative said handle from a first position to a second position, and a V-spring having one portion fixedly coupled to said second portion of said trigger means, and having a second portion with a free end, wherein
movement of said trigger means from said first position to said second position causes said free end of said V-spring to push on a first seat of said proximal portion of said plunger and push said plunger distally a first predetermined distance, and movement of said trigger means from said second position to said first position causes said free end of said V-spring to ride over an adjacent ramp of said proximal portion of said plunger and to set in a second seat of said proximal portion of said plunger.

18. An endoscopic tool according to claim 17, wherein:
each said ramp has an axial length substantially equal to the length of the unit of hemostatic agent.

19. A surgical method for applying units of a hemostatic agent to an internal bleeding site using an endoscopic tool loaded with a plurality of discrete individual units of hemostatic agent said discrete individual units being of substantially identical size to each other, said endoscopic tool having a hollow tube which holds the plurality of discrete individual units of the hemostatic agent, said hollow tube having proximal and distal ends with an opening in said distal end, a plunger which extends into the hollow tube and contacts a proximal unit of the hemostatic agent, and hand actuated movement means coupled to said plunger for moving said plunger distally in measured incremental movements, wherein said plunger and said hand actuated movement means together comprise ratchet means having means for preventing proximal movement of said plunger upon each said incremental movement, said method comprising:
a) inserting said endoscopic tool in a trocar tube and positioning said endoscopic tool at a bleeding site;
b) actuating said hand actuated movement means a first time to move said plunger distally in a first incremental movement, thereby discharging a first discrete individual unit of said hemostatic agent through said opening in said distal end of said hollow tube; and
c) actuating said hand actuated movement means a second time to move said plunger distally in a second incremental movement, thereby discharging a second discrete individual unit of said hemostatic agent through said opening in said distal end of said hollow tube, said second discrete individual unit being substantially the same size as the first discrete individual unit.

* * * * *